United States Patent [19]
Kamm et al.

[11] Patent Number: 6,117,087
[45] Date of Patent: Sep. 12, 2000

[54] METHOD AND APPARATUS FOR NONINVASIVE ASSESSMENT OF A SUBJECT'S CARDIOVASCULAR SYSTEM

[75] Inventors: Roger D. Kamm, Weston; Edwin Tomoya Ozawa, Cambridge, both of Mass.

[73] Assignee: Massachusetts Institute of Technology, Cambridge, Mass.

[21] Appl. No.: 09/053,369

[22] Filed: Apr. 1, 1998

[51] Int. Cl.[7] ........................................ A61B 5/00
[52] U.S. Cl. ..................... 600/504; 600/500; 600/481
[58] Field of Search ........................... 600/500–504, 600/481–466, 300; 128/920–925, 900

[56] References Cited

U.S. PATENT DOCUMENTS

| | | |
|---|---|---|
| 4,993,420 | 2/1991 | Welkowitz et al. . |
| 5,054,493 | 10/1991 | Cohn et al. . |
| 5,101,828 | 4/1992 | Welkowitz et al. . |
| 5,211,177 | 5/1993 | Chesney et al. . |
| 5,265,011 | 11/1993 | O'Rourke . |
| 5,265,615 | 11/1993 | Frank et al. . |
| 5,277,188 | 1/1994 | Selker ...................................... 600/508 |
| 5,277,189 | 1/1994 | Jacobs ...................................... 600/508 |
| 5,282,474 | 2/1994 | Valdes Sosa et al. .................. 600/483 |
| 5,316,004 | 5/1994 | Chesney et al. . |
| 5,390,679 | 2/1995 | Martin ...................................... 600/486 |
| 5,400,793 | 3/1995 | Wesseling . |
| 5,406,952 | 4/1995 | Barnes et al. . |
| 5,533,511 | 7/1996 | Kaspari et al. . |
| 5,535,753 | 7/1996 | Petrucelli et al. . |
| 5,647,369 | 7/1997 | Petrucelli et al. . |
| 5,724,983 | 3/1998 | Selker et al. ............................ 600/301 |
| 5,797,395 | 8/1998 | Martin ...................................... 600/486 |

*Primary Examiner*—Cary O'Connor
*Assistant Examiner*—Michael Astorino
*Attorney, Agent, or Firm*—Bromberg & Sunstein LLP

[57] ABSTRACT

A method and apparatus for deriving a physiological description and clinically-useful data reboarding the cardiovascular system of an individual subject. The method includes obtaining a measurement sample associated with cardiovascular flow and utilizing a model, which may be distributed and/or non-linear to derive a description and data. The model generates and uses functions of source parameters and may, in an embodiment, match measurement samples against a library of stored predicted samples. A best-matching, predicted sample may then be associated with a measurement sample. An apparatus is provided which, according to an embodiment, includes an input for obtaining a measurement sample, a processor to derive the description and data, and an output. The apparatus may also include a digital storage medium to store a library of predicted samples.

16 Claims, 7 Drawing Sheets

PRIOR ART

METHOD AND APPARATUS FOR NONINVASIVE ASSESSMENT OF A SUBJECT'S CARDIOVASCULAR SYSTEM

TECHNICAL FIELD

The present invention relates to the modeling of cardiovascular systems and the prediction of clinically-useful data regarding the cardiovascular system of an individual subject.

SUMMARY OF THE INVENTION

The invention provides, in accordance with a specific embodiment, a method of deriving a physiological description of a cardiovascular system. In this embodiment, a step involves obtaining a measurement sample associated with the flow of the cardiovascular system. The embodiment also includes the step of utilizing a model that predicts measurement values associated with cardiovascular blood flow as a function of a plurality of source parameters to derive a physiological description of the cardiovascular system in terms of at least one of the source parameters. As used in this description and in the following claims, the phrase "measurement value associated with cardiovascular blood flow" is defined to include a value associated with any of the following characteristics or a function of any one or more of the following characteristics: pressure, volume flow rate, velocity, and vessel cross-sectional area. As used in this description and in the following claims, the term "model" is defined as a mathematical construct developed utilizing the physical principles of fluid dynamics. The definition of the term "model" does not extend to empirically-based constructs which are not, therefore, predictive from first principles. The model may be distributed, non-linear or both. As used in this description and in the following, claims, the term "distributed" excludes modeling simply as a linear transmission line. In accordance with a related embodiment, there is provided a method of deriving a physiological description of a cardiovascular system, wherein the method includes obtaining a measurement sample associated with flow of the cardiovascular system, matching the measurement sample against a library of stored predicted samples, each predicted sample derived from a model of the cardiovascular system and associated with a set of source parameter values, the set having at least one source parameter value, in order to identify a best-matching predicted sample, and associating the measurement sample with the set that is associated with the best-matching predicted sample.

In accordance with other embodiments, the set of source parameters may include a measure of heart compliance during its contraction, a measure of systemic vascular resistance and a measure of cardiac output. The step of matching may further include a score determination which analyzes the closeness of match and selects the best-matching sample based on the score.

In accordance with another embodiment, the invention provides an apparatus for deriving a physiological description of a cardiovascular system. In the embodiment, the invention includes an input for receiving a measurement sample associated with flow of the cardiovascular system, a processor coupled to the input, and an output. The processor utilizes a model that predicts measurement values associated with cardiovascular blood flow as a function of a plurality of source parameters for deriving the value of at least one source parameter pertinent to a physiological description of the cardiovascular system. The output specifies the value of the at least one source parameter. The model is either distributed, or non-linear, or both.

Another embodiment of the apparatus includes an input for receiving a measurement sample associated with flow of the cardiovascular system and a digital storage medium for storing a library of predicted samples. Each predicted sample is derived from a model of the cardiovascular system and associated with a set of source parameter values. The set has at least one source parameter value. The apparatus also includes a processor, coupled to the input and having access to the digital storage medium, for matching the measurement sample against the library of predicted samples, to identify a best-matching predicted sample, and an output for identifying at least one member of the set of source parameters values associated with the best-matching predicted sample. In a related embodiment the processor includes an arrangement for determining closeness of match scores as described above.

As in the case of methods described above, in accordance with further embodiments of the apparatus, the set of source parameters may include a measure of heart compliance during its contraction, a measure of systemic vascular resistance and a measure of cardiac output. The step of matching may further include a score determination which analyses the closeness of match and selects the best-matching sample based on the score.

DETAILED DESCRIPTION OF SPECIFIC EMBODIMENTS

Introduction. Arterial pressure and flow pulses clearly reflect differences between normal and pathological states. These differences are based on such factors as arterial geometry, peripheral resistance, and cardiac contractility. Thus, the potential exists to extract clinically useful data from analysis of the shape, magnitude, and timing of the pulse. The premise behind this invention is that changes in the pressure pulse are indicative of changes in the hemodynamic state of the patient and that quantitative analysis of the pressure and/or flow traces can provide estimates of important hemodynamic parameters. A numerical model can provide the means for understanding the connection between the measured arterial pulse and the hemodynamic parameters. Such an algorithm may be easily integrated into standard hospital monitoring techniques, thus potentially reducing the need for traditional, more invasive, hemodynamic monitoring methods.

This invention provides in a preferred embodiment, a method and apparatus for continuous monitoring of the hemodynamic state of a subject, either at home or in the hospital. It makes use of recently developed computational methods for simulating the cardiovascular system with a realistic model, capable of predicting with great accuracy the time-varying pressure and flow traces throughout the arterial network. It also utilizes methods of parameter estimation based on comparison between measured pressure or flow traces and the corresponding traces produced by the computational model and stored in a database. The method requires only a single measurement of the pressure or flow trace at one easily accessible location in the arterial system and has the potential for making detailed predictions of many patient parameters of clinical importance. Among these are peripheral resistance, arterial elastance, cardiac contractility, diastolic filling volume and cardiac output. The measurement can be made by using a sensing device worn by the subject as a wrist watch or ring with a signal sent by telemetry to a remote receiver for analysis. The result of the analysis could be a warning sent either to the subject or directly to the physician or hospital in the event that one or more parameter values deviate from normal range. Alternatively, the results could simply provide a means of observing normal variations in the hemodynamic state of the subject over time.

There is increasing pressure on the medical profession to provide quality health care at low cost. There is also a compelling need to minimize the length of hospitalization, increasing, the need for home health care monitoring equipment. Finally, as the population ages, the incidence of diseases of the elderly, heart disease being among the most prevalent, will continue to increase.

At the same time, computational methods and computational hardware continue to advance at rapid rates. Methods now exist to simulate the entire cardiovascular system with great detail. These methods have the capability of simulating subject-specific behavior simply by unique specification of the many parameters of the model. Finally, noninvasive methods and devices for monitoring the time-varying pressure or flow traces at different locations in the arterial network are currently available and others are under development.

This sets the stage for embodiments of the present invention which combines current computational methods and solutions obtained by high-speed workstations with readily obtained measurements on a particular subject. Recognizing that the detailed pattern of the pressure or flow trace represents a unique combination of the parameters characterizing the patient (suitably reduced to become tractable), it is possible to inter clinically-useful information from a comparison of a measurement to the solutions obtained from the computer simulation. This invention represents a method for doing so.

Embodiments of this invention utilize a computational model of sufficient realism and complexity to capture the behavior of the real cardiovascular system. Solutions obtained from this model using a high-speed computer in which a carefully selected subset of the entire parameter set that govern system behavior have been systematically varied are stored in a database or library for later use. Solutions obtained from this model are represented in terms of a collection of "features" that capture the essential character of the computed pressure or flow traces. These features are expressed in mathematical form as functions (surrogates) of the several dominant parameters and used to assist in the parameter estimation procedure.

The estimation of cardiovascular parameters for a particular subject is based on a comparison of a measured flow or pressure trace from the individual to the many solutions contained in the library to identify the closest match. This can be accomplished in a variety of ways, but in the preferred embodiment, is done by solution of the surrogate equations based on the features extracted from the measured trace.

This invention also provides in a preferred embodiment a method for and device for measuring the pressure or flow trace of an individual and cardiovascular system and either storing the trace for later analysis, analyzing the trace immediately and storing its features, or sending, by telemetry, the trace or features to a remote site for further analysis. Analysis involves comparing the measured trace with the traces contained in the library, predicted by the computer model, to determine the one that best tits the measurement. This may be accomplished by extracting the features from the curve and using these features, along with the mathematical functions described above, to solve for the corresponding parameter,values, or by direct comparison of the measured trace with the computed ones, using any of a number of pattern recognition methods to identify the best flit.

The present invention provides a preferred embodiment, a method and apparatus for determining clinically-useful parameters of a subject's cardiovascular system. This method employs a non-linear, distributed model of the arterial system and heart to generate a database (library) of Solutions, each corresponding to a different set of model parameters. In this embodiment, one or several noninvasive measurements are made of the subject's arterial flow or pressure at easily accessible locations such as the radial or brachial artery. System identification techniques are then applied to determine which of the solutions in the library most closely matches the measurement. The parameters used to (generate this closest match solution provide a means of evaluating the cardiovascular health of the patient.

In a further embodiment, a set of six most influential governing model parameters are identified through a sensitivity analysis of all model parameters, followed by model simplification and non-dimensionalization. A library of simulation data is then constructed using for example 337 runs of the model, varying each of the parameters independently over discrete grid points in the six-dimensional space. The parameter estimation scheme makes use of the parameter space-containing library to construct surrogates (approximations of the actual functions) to describe the behavior of "features" extracted from the computed waveforms at each grid point. Thus, if a feature set is determined from the measured patient waveforms, the surrogate equations can then be solved iteratively to determine the six unknowns (system parameters) unique to the specified feature set.

A method and apparatus for determining clinically-useful parameters of a subject's cardiovascular system. The method employs a non-linear, distributed model of the arterial system and heart to generate a database (library) of solutions, each corresponding to a different set of model parameters. One or several noninvasive measurements are made of the subject's arterial flow or pressure at easily accessible locations such as the radial or brachial artery. System identification techniques are then applied to determine which of the solutions in the library most closely matches the measurement. The parameters used to generate this closest match solution provide a means of evaluating the cardiovascular health of the patient.

In one particular embodiment, a set of six most influential governing model parameters were identified through a sensitivity analysis of all model parameters, followed by model simplification and non-dimensionalization. A library of simulation data was then constructed using 337 runs of the model, varying each of the parameters independently over discrete grid points in the six-dimensional space. The parameter estimation scheme makes use of the parameter space-containing library to construct surrogates (approximations of the actual functions) to describe the behavior of "features" extracted from the computed waveforms at each grid point. Thus, if a feature set is determined from the measured patient wavefroms, the surrogate equations can then be solved iteratively to determine the six unknowns (system parameters) unique to the specified feature set.

1. The Computational Model. Before describing the equations used to construct the numerical model, it is useful to identify the primary modeling assumptions. The following list is similar to that made previously by Stettler and co-workers (Stettler et al., 1981) in the construction of their distributed model:

- Blood is approximated as an incompressible, Newtonian fluid.
- Blood flow in the aortic tree is approximately one-dimensional, justified by the unidirectional, primarily axial nature of blood how in arteries (Pedley, 01980).
- The artery walls may be treated using a viscoelastic model.
- Viscous friction is approximated by considering the periodic behavior of wall shear, when appropriate.
- Curvature is ignored. The segments arc assumed to be linearly tapered with respect to the cross-sectional area between bifurcation regions, and the angle of departure of a daughter branch from the main branch and the additional losses associated with the branched flow are taken into account.
- Flow into minor branches may be treated as a distributed leakage. This leakage is a function of the arterial-venous pressure gradient.

The analysis begins with consideration one dimensional flow in an elastic artery using the basic equations for momentum and continuity:

$$\frac{\partial u}{\partial t} + \frac{\partial}{\partial x}\left(\frac{u^2}{2} + \frac{P}{\rho}\right) + F = 0 \tag{1}$$

$$\frac{\partial A}{\partial t} + \frac{\partial}{\partial x}(uA) + \Psi = 0 \tag{2}$$

where u and P are the cross-sectional average velocity and pressure, A is the cross-sectional area at any axial location within an element, and F is the frictional loss, to be described later in further detail. The leakage term $\Psi$ in the continuity expression represents the distributed wall leakage per unit length. This term can be approximated as a linear resistive element described by the equation $$\Psi(P, z) = \Phi(z)(P - P_V) \tag{3}$$

where the driving force for flow is the pressure drop between the local arterial pressure and the uniform venous pressure $P_v$. The equations of motion (1) and (2) can be reduced to matrix from:

$$\frac{\partial}{\partial t}[A] + \frac{\partial}{\partial x}[B] + [C] = 0 \tag{4}$$

where $$[A] = \begin{bmatrix} u \\ A \end{bmatrix}, [B] = \begin{bmatrix} u^2/2 + P/\rho \\ uA \end{bmatrix}, \text{ and } [C] = \begin{bmatrix} F \\ \Psi \end{bmatrix} \tag{5), (6), (7}$$

A pressure-area relation or "tube law" may be formulated to provide a third independent equation. This relationship will be described in further detail below. The set of hyperbolic. partial differential equations (4) for the elements are solved using, an adaptation of the MacCormack two step predictor-corrector method (Kimmel, 988).

For large values of the Womersley number the assumption of fully-developed viscous flow is inappropriate. As the frequency rises, the magnitude of the wall shear stress increases and there develops a significant phase lag between the axial velocity and the friction force. A more realistic approximation of the frictional losses in periodic flow was developed by Zeilke (Zeilke, 1968) based on the one-dimensional momentum equation in cylindrical coordinates:

$$\mu \frac{\partial^2 u}{\partial r^2} + \frac{1}{r}\frac{\partial u}{\partial r} - \frac{1}{u}\frac{\partial u}{\partial t} = \frac{1}{u\rho}\frac{\partial P}{\partial x}, \tag{8}$$

where it is assumed that the convective acceleration term does not affect significantly the axial velocity profile. Taking the Laplace transform of the momentum equation, the velocity it can be determined in the Laplace domain, subject to the boundary conditions u=0 at r=R, and du/dt =0 at r=0 in a tube of radius R. The inverse Laplace transform of the wall shear stress yields a relationship in the form of a convolution integral $$T(t) = \int_0^\infty u\dot{Y}(t')W(t-t')dt'. \tag{9}$$

The term W(t) is represented by two separate functions (Zeilke. 1968):

$$W(t) = e^{-26.3774\mu\frac{t}{\rho R^2}} + e^{-70.8493\mu\frac{t}{\rho R^2}} + \\ e^{-135.0198\mu\frac{t}{\rho R^2}} + e^{-218.9216\mu\frac{t}{\rho R^2}} + e^{-322.5544\mu\frac{t}{\rho R^2}} \tag{10}$$

when $\frac{\mu t}{\rho R^2} > 0.02$ and $$W(t) = 0.282095\left(\frac{\mu t}{\rho R^2}\right)^{-1/2} - 1.250000 + 1.057855\left(\frac{\mu t}{\rho R^2}\right)^{1/2} + \\ 0.937500\frac{\mu t}{\rho R^2} + 0.396696\left(\frac{\mu t}{\rho R^2}\right)^{3/2} - 0.351563\left(\frac{\mu t}{\rho R^2}\right)^2$$

when $\frac{\mu t}{\rho R^2} \leq 0.02$.

Substituting for the friction term F in equation (1) yields the final form of the momentum equation:

$$\frac{\partial u}{\partial t} + \frac{\partial}{\partial x}\left(\frac{u^2}{2} + \frac{P}{\rho}\right) + \frac{2\pi\mu}{\rho A}\left(4u(t) + 2\int_0^\infty u\dot{Y}(t')W(t-t')dt'\right) = 0 \quad (11)$$

Note that this frequency dependence on friction has been used in previously published cardiovascular models (Stettler, 1981).

We include viscoelastic damping in formulating an expression for the tube law, using the analysis presented by Holenstein et al. (Holenstein, 1980). From linear viscoelastic theory, a relationship between stress and strain may be written as a convolution integral. This results in the following expression:

$$A(t) = A^e(P(t)) + \int_0^\infty J^{\dot{Y}}(t')A^e(t')A^e(P(t-t'))dt' \quad (12)$$

where $$J^{\dot{Y}}(t)$$

is the time derivative of the creep function for the arterial wall, and $A^e$ is the instantaneous cross-sectional area of the artery after a step function in pressure is applied. As with the transient wall shear, the wall viscoelasticity is dependent on the area history. Holenstein et al, use the following creep function (Fung, 1972):

$$J(t) = 1 + a\log\frac{\tau_2}{\tau_1} + a\left(E_1\left(\frac{t}{\tau_1}\right) - E_1\left(\frac{t}{\tau_2}\right)\right) \quad (13)$$

where $$E_1(z) = \int_z^\infty \frac{e^{-t}}{t}dt. \quad (14)$$

The coefficients are specified as:
 a=0.3
 $t_1$=0.00081 sec $^{-1}$
 $t_2$=0.41 sec $^{-1}$.
and are obtained from experimental data (Niederer, 1985). This results in the following time derivative of the creep function used in the convolution, $$J^{\dot{Y}}(t) = a\frac{e^{-t/\tau_2} - e^{-t/\tau_1}}{t}. \quad (15)$$

given that the expression for the instantaneous elastic response takes the form:

$$A^e = A_o^e(p_o, z) \cdot \exp\left(\frac{p - p_o}{\rho \cdot c(p_o, z) \cdot c(p, z)}\right) \quad (16)$$

An estimate of the wave speed in an artery segment can be obtained using, the following expression derived by Stettler:

$$c(P,x) = (X_0 + B(P - P_e)) \cdot g(z) \quad (17)$$

where the constants B=1.5×10$^{-3}$ g/sec cm$^2$ and c0=140cm/sec, and are obtained from experimental measurements (Stettler et al., 1981). The function g(z) is obtained by equating, the reference wave speed $c_0$ at position z to the right hand side of equation (17), given P=$P_e$, and solving for g(z). The calculation of $c_0$ is outlined in a later section on the standard case. The expression (12) can be solved for using equations (15) and (16) to provide a relationship between pressure and area at a given node.

The individual arterial segments are coupled through appropriate boundary conditions. both internally at the bifurcations, and externally at the left ventricle and the terminal arterioles. Consider first the coupling of several elements at a bifurcation, defined as a single tube branching into separate daughter tubes. Choosing a control volume corresponding to a stream tube that includes all of the flow entering the nth daughter branch, and assuming that the area of that stream tube in the parent branch is $U_n A_n | U_1$, the equation of energy conservation may be written as (Wolf. 1990):

$$\rho\frac{\partial U_1}{\partial t}x_1 + \rho\frac{\partial U_n}{\partial t}x_n + P_n + \frac{f}{2}\rho U_n^2 + \frac{\Phi_{1n}}{A_n} = P_1 + \frac{1}{2}\rho U_1^2 \quad (18)$$

where "1" denotes the upstream boundary in the parent branch and "n" denotes the downstream boundary in one of the N−1 daughter branches. The term f in equation (18) represents the ratio of actual kinetic energy flux at M to that corresponding to a flat velocity profile:

$$f = \frac{1}{A}\int\left(\frac{u}{U}\right)^3 dA \quad (19)$$

and is assumed to be equal to unity in the parent branch. Additionally, $\Phi_{1n}$ represents the frictional dissipation rate. The losses will be described in more detail shortly. The unsteady continuity equation for the control volume encompassing the entire bifurcation including all daughter vessels is:

$$\frac{\partial A_1}{\partial t}x_1 + \frac{\partial A_2}{\partial t}x_2 + \ldots + \frac{\partial A_N}{\partial t}x_N - U_1A_1 + U_2A_2 + \ldots + U_NA_N = 0 \quad (20)$$

The equations of motion can he coupled with momentum and continuity between the interface of an element with the bifurcation control volume, and the element's interior points. Thus, at each interface there are three unknown values: pressure, velocity, and cross-sectional area. An additional equation that is not shown is the pressure-area relationship for the bifurcation including wall viscoelasticity, similar in form to relationship (12).

Dissipation within the bifurcation is a complex function of the geometry and flow conditions, depending for example on whether or not flow separation exists. In the absence of flow separation frictional losses are likely to scale in a manner similar to an entrance region or a curved tube, as suggested by Pedley (Pedley, 1970) and Collins et al. (Collins, 1993). In both cases, the dissipation rate scales as $$U^{5/2}$$

In the presence of additional losses due to separation and turbulence, the dissipation rate would scale as $$U^3$$

These scaling relationships sugtrest the following form:

$$\Phi_{1n} = \left(\frac{1}{2}\rho U_1^{1/2} A_n\right)\lambda_n U_n^{5/2} + \frac{1}{2}\rho U_n^3 A_n k_n \quad (21)$$

where $\lambda_n$ and $\kappa_n$ are dimensionless head loss coefficients due to "entrance type" and "turbulent type" losses, respectively. The other term in parentheses is introduced in order to make $\lambda_n$ dimensionless. Followinig Pedley (Pedley. 1970), $\lambda_n$ is given by:

$$\lambda_n = \frac{16C}{\sqrt{2}}\left[\frac{1}{Re_1}\frac{D_1}{D_n}\frac{L_n}{D_n}\right]^{1/2} \quad (22)$$

where $Re_1$ is the Reynolds number of the parent branch. Equations (19) and (21) may he incorporated into the energy conservation equation (18). The resulting energy equation has the following final form:

$$\rho\frac{\partial U_1}{\partial t}x_1 + \rho\frac{\partial U_N}{\partial t}x_n + P_n + \frac{1}{2}\rho(U_n^2 f_n + U_n|U_n|k_n) - \quad (23)$$

$$P_1 - \frac{1}{2}\rho U_1^2 + \frac{1}{2}\rho U_n|U_1 U_n|^{1/2}\lambda_n = 0$$

The absolute values of velocity are incorporated to preserve the directionality of the losses as the flow changes direction.

The values of the kinetic energy and dissipation factors are dependent on the nature of flow at the bifurcation. For highly symmetric bifurcation regions with two daughter branches departing at small angles from each other, one would expect little flow separation and hence little energy dissipation due to turbulence and distortion of the axial velocity profile. In this limit of unseparated flow, the factor κ should approach zero and κ should approach 1, which is borne out by the definitions of the Factors as given by Woll(1990):

$$k = \left(1 - \frac{1}{K_c}\right)^2 \text{ and } f = \left(\frac{1}{K_c}\right)^2 \quad (24), (25)$$

The contraction coellicient $K_c$ represents the ratio between the minimum normal cross-sectional area of the stream tube within the separated region of the daughter branch, and the area of the branch itself. Hence, for smaller angles between adjacent daughter branches, separation does not occur and $K_c$ should approach 1. If we now consider the case in which a highly asymmetric daughter branch departs from the main conduit at a large angle, then the limit of highly separated flow is reached and $K_c$ approaches zero, resulting in large kinetic energy coefficients. Furthermore, it is appropriate to neglect 1 in the limit of high flow separation. For computational purposes, both $K_c$ and 1 are assumed constant through time for each specific bifurcation branch. Based on anatomical branching angles of the arterial system, a linear relationship between angle and $K_c$ can be made and values assigned for each branch. Variation of the contraction coefficients has demonstrated that exact values are not required due to their small effect on the system as a whole. The equation of energy (23), and the unsteady form of continuity (20) are solved by combining them with the MacCormack predictor-corrector computational scheme to couple the state variables of the end nodes with the internal points.

A model of the left ventricle acts as an upstream boundary for the arterial tree. The ventricle may be approximated as a chamber whose compliance (the inverse of elastance) changes with time, thus driving flow through a unidirectional exit (aortic) valve. A single cycle of the left ventricle can be subdivided into four parts: 1) early systole, during which time the pressure in the left ventricle begins to rise towards arterial levels as a result of increasing ventricular wall stiffness; 2) the ejection phase of systole, when ventricular pressure exceeds aortic pressure, causing the aortic valve to open and the ventricle to empty, 3) flow reversal, where pressure in the left ventricle drops below aortic pressure, causing blood to accelerate backwards to close the aortic valves and fill the sinuses of valsalva; 4) diastole, during which the left ventricle fills to end-diastolic volume, and the velocity at the aortic root is zero.

The elastance curve E(t) is of importance in determining the shape of the forward pressure wave. Additionally, changes in the strength of contraction due to impaired myocardium in heart failure can be modeled as changes in this curve. Extensive studies of the pressure-volume relationship in canine ventricles (Suga and Sugawa, 1974) have shown that the basic shape of the systolic portion of the pressure-volume curve remains unchanged, regardless of loading or inotropic changes. Thus, the systolic wall elastance may be characterized by only two parameters: the maximum wall elastance $E_{max}$, and time to peak elastance $T_{max}$. The total length of the cycle is extrapolated from Suga and Sugawa's data suggestin, that $T_{max}$ spans approximately 30–50% of the total cycle.

For the purposes of our model, we have found that the following form provides sufficient modeling of the physics to give realistic results:

$$P_{vent} = E^*(t) \cdot (V_{vent} - V_{vent,o}) \cdot \left(1 - \sigma\left(-\frac{dV_{vent}}{dt}\right)\right) + P_{tp} \quad (26)$$

The coefficients is a scaling factor for the time-dependent effects, $V_{vent}$ is ventricular volume. $V_{vent,o}$ is the zero-pressure filling volume, and $P_{tp}$ is the transpulmonary pressure which is expected to alter the left ventricular. The isovolumetric contraction curve E*(t) is assumed to be a halt sinusoid, whose duration is defined by the systolic to cycle time ratio. Thus, the ventricular pressure may be solved for, given that the flow rate at the root of the aorta is equal to the time derivative of ventricular volume.

The numerical model described here allows for linear segments that represent the larger vessels in the arterial tree, but to model the liner terminal branching structure in this manner is impractical. Rather, the terminal vessels are modeled as a lumped parameter Windkessel, using a form derived by previous investigators (Berger et al., 1994: Burger et al., 1995). The model is advantageous in that it allows the behavior of an entire arteriolar and small vessel bed to be captured using few parameters. It is also advantageous in that the phenomenon of peripheral wave reflections is well approximated. The Windkessel consists of a resistance $R_s$ in parallel with a compliance $C_s$ where the resistance represents the pressure drop associated with constriction of the arteriolar smooth muscle, and $C_s$ represents the total compliance of the small artery network. In series with the Windkessel is an additional element $Z_0$, which represents the entrance impedance of the parent branch which the boundary condition is attached to. approximated as rc/A. From the electrical analog, the following equations may be written as a function of the resistances and capacitances:

$$\frac{P_c - P_v}{R_s} + C_s \frac{dP_c}{dt} = Q \tag{27}$$

$$Q = \frac{1}{Z_o}(P - P_c) \tag{28}$$

where Q is flow entering the Windkessel passing through $Z_0$. The Windkessel is coupled numerically to the parent segment in this model using the method of characteristics.

Figure 2:
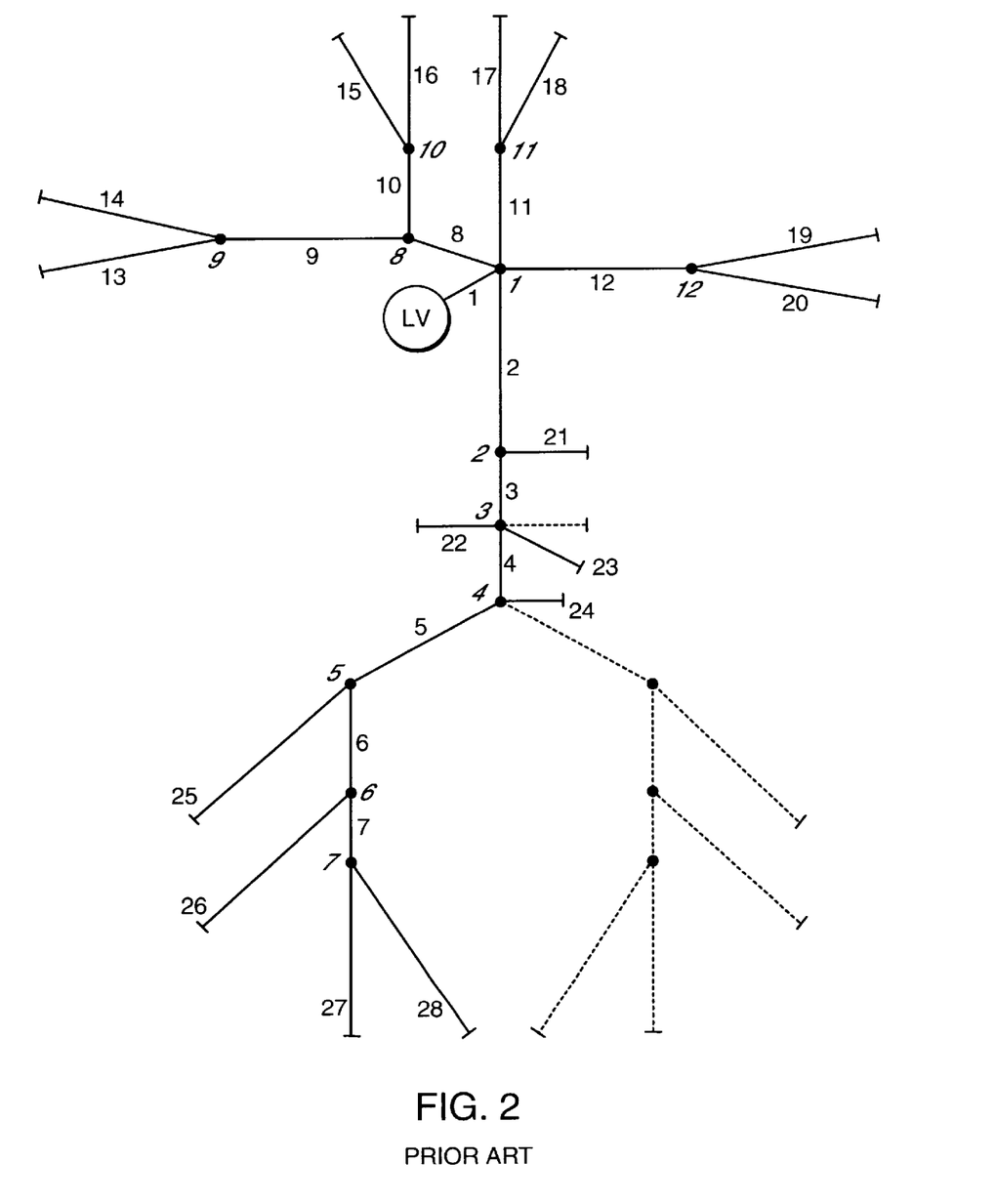
FIG. 2 depicts a twenty-eight element distributed model of the arterial system.
Figure 3A:
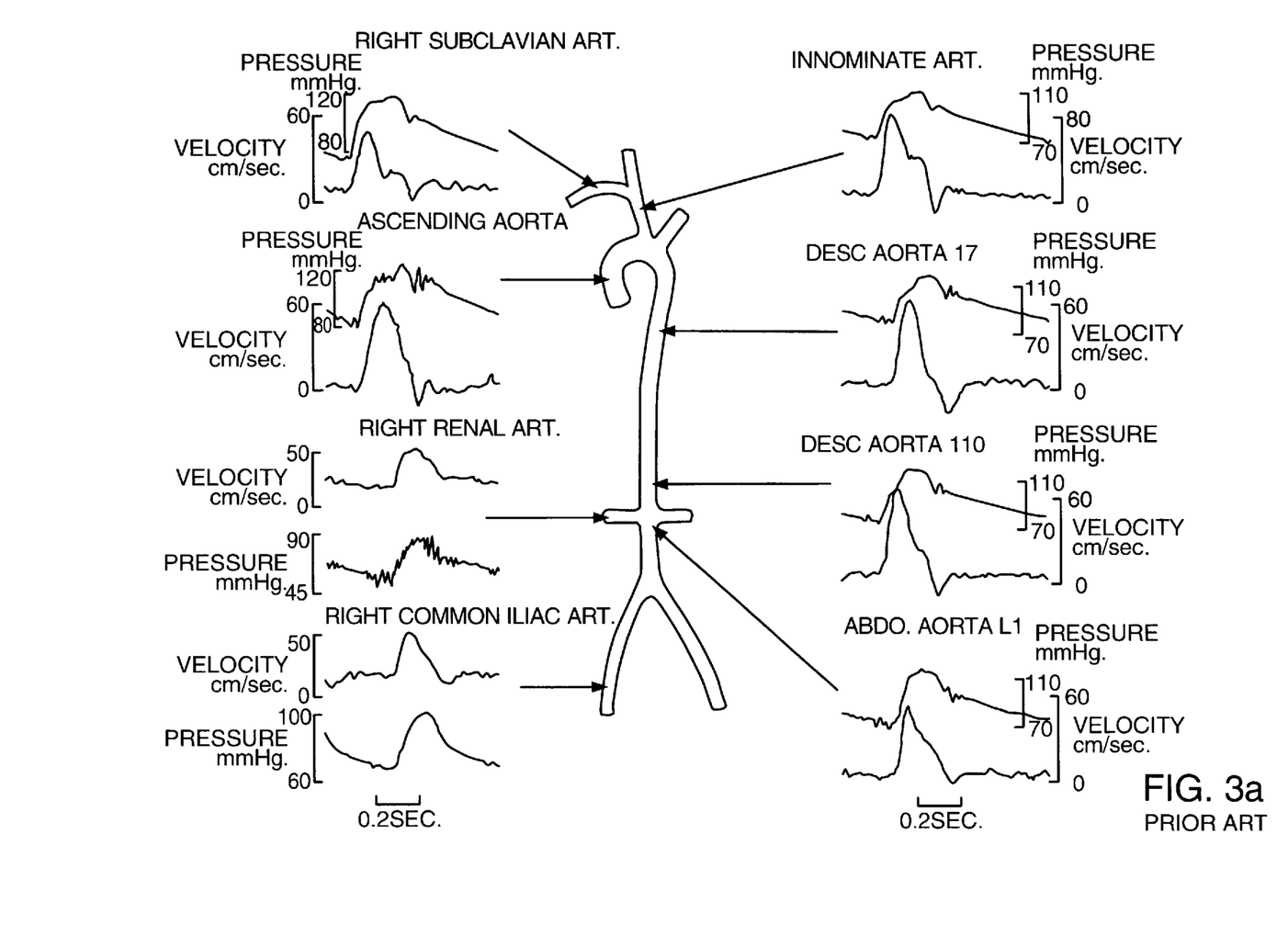
FIGS. 3a and 3b are representations of simultaneous pressure and blood velocity patterns.
Figure 3B:
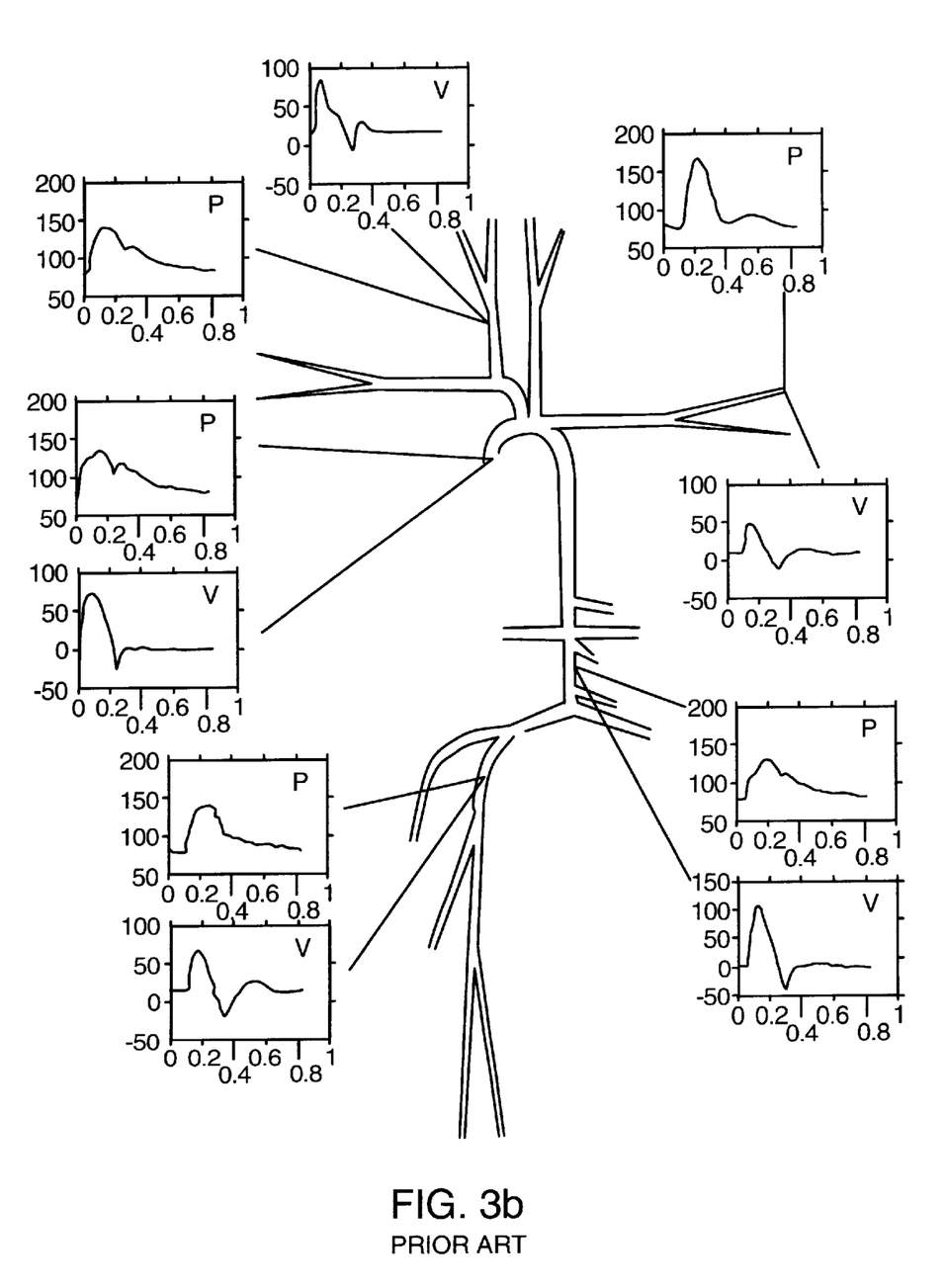

The arterial tree is represented by a network consisting of twenty-eight elements shown schematically in FIG. 2. Each element is assigned a number as is each bifurcation. The numbered elements correspond to specific major arteries. Values for the various parameters of the model were taken from the literature or estimated based on available knowledge as described in Ozawa (1996). The values used as the "standard case" from which variations are made as described below are given in Tables 1 & 2. Using these values, the validity of the model can be assessed by comparing simulation results to measurements from the literature. One such sample comparison is illustrated in FIGS. 3a and 3b between calculations using the standard case parameter values and measurements of Mills et al. (1970). For other validation results, see Ozawa (1996).

TABLE 1

Specifications for the 28 element model: arterial properties.

| element # | artery name | element type | length (cm) | proximal area (cm$^2$) | distal area (cm$^2$) | E × 10$^6$ (dyn/cm) | K (sec$^{-1}$) |
|---|---|---|---|---|---|---|---|
| 1 | ascending aorta | 1 | 5.5 | 6.605 | 3.941 | 4.0 | 0 |
| 2 | thoracic aorta | 0 | 18.5 | 3.597 | 2.835 | 4.0 | 0 |
| 3 | abdominal aorta | 0 | 4.3 | 2.378 | 2.378 | 4.0 | 0 |
| 4 | abdominal aorta | 0 | 9.6 | 1.021 | 1.021 | 4.0 | 0 |
| 5 | common iliac | 0 | 19.2 | 0.849 | 0.229 | 4.0 | 0 |
| 6 | femoral artery | 0 | 43.2 | 0.181 | 0.126 | 8.0 | 294 |
| 7 | anterior tibial artery | 0 | 1.5 | 0.053 | 0.053 | 16.0 | 294 |
| 8 | brachiocephalic | 0 | 2.4 | 1.208 | 1.208 | 4.0 | 0 |
| 9 | r brachial | 0 | 41 | 0.503 | 0.181 | 4.0 | 196 |
| 10 | r common carotid | 0 | 16.8 | 0.503 | 0.503 | 4.0 | 0 |
| 11 | l common carotid | 0 | 11 | 0.503 | 0.503 | 4.0 | 0 |
| 12 | l brachial | 0 | 44.4 | 0.554 | 0.181 | 4.0 | 196 |
| 13 | r radial | 2 | 23.2 | 0.08 | 0.08 | 8.0 | 294 |
| 14 | r ulnar | 2 | 22.9 | 0.139 | 0.113 | 8.0 | 294 |
| 15 | r external carotid | 2 | 11.3 | 0.196 | 0.071 | 8.0 | 294 |
| 16 | r internal carotid | 2 | 17.2 | 0.283 | 0.053 | 8.0 | 196 |
| 17 | l internal carotid | 2 | 17.2 | 0.283 | 0.053 | 8.0 | 196 |
| 18 | l external carotid | 2 | 11.3 | 2.196 | 0.071 | 8.0 | 294 |
| 19 | r radial | 2 | 23.2 | 0.139 | 0.113 | 8.0 | 294 |
| 20 | r ulnar | 2 | 22.9 | 0.08 | 0.08 | 8.0 | 294 |
| 21 | coeliac | 2 | 1 | 0.478 | 0.478 | 4.0 | 196 |
| 22 | renal | 2 | 2.7 | 0.212 | 0.212 | 4.0 | 294 |
| 23 | sup mesenteric | 2 | 5.4 | 0.581 | 0.581 | 4.0 | 196 |
| 24 | inf mesenteric | 2 | 4.5 | 0.08 | 0.08 | 4.0 | 294 |
| 25 | profundis | 2 | 12.1 | 0.166 | 0.166 | 16.0 | 294 |
| 26 | post tibial | 2 | 30.6 | 0.102 | 0.102 | 16.0 | 294 |
| 27 | ant tibial | 2 | 29.5 | 0.031 | 0.031 | 16.0 | 294 |
| 28 | peroneal | 2 | 31.3 | 0.053 | 0.053 | 16.0 | 294 |

Figure 1:
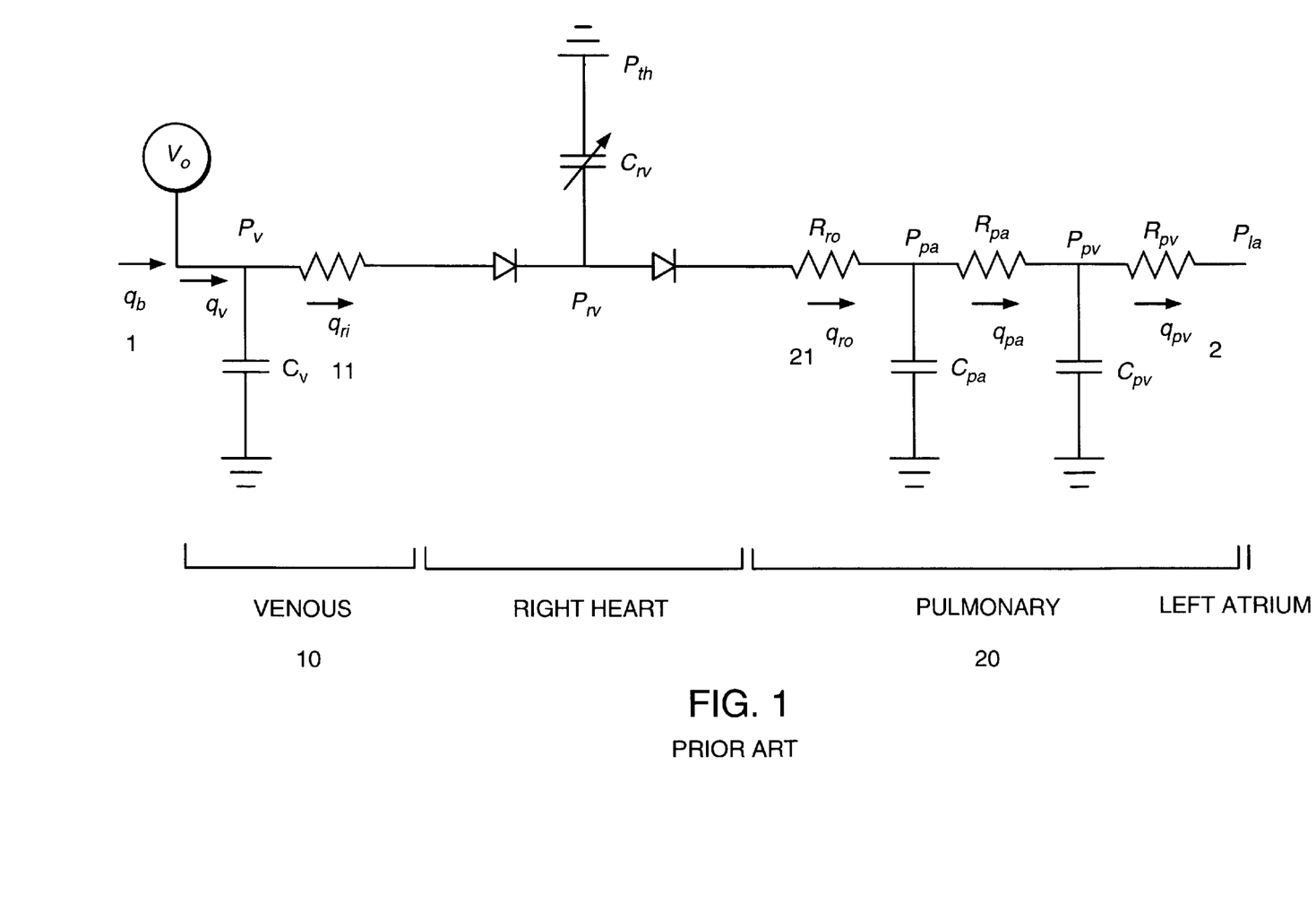
FIG. 1 is a schematic representation of the venous and pulmonary circulation as an electrical circuit analog.

Since we are primarily interested in the behavior of the arterial system, the venous 10 and pulmonary 20circulations are modeled as lumped parameters shown schematically in FIG. 1, rather than as a distributed branching model used for the arterial side. Note that the model contains unidirectional valves for entry 11 of blood into and exit 21 of blood into the right ventricle, which is also driven by a specified time-varying compliance. Venous inflow from the capillary beds $q_b$ 1 is obtained by summing the total outflow from the arterial system: the flow rate to the left atrium $q_{pv}$ 2is calculated from the left ventricular model outlined above. For the present model the effect of respiration is neglected and thoracic pressure is assumed constant. The first order differential equations that govern the lumped parameter model may be solved with a fourth-order Runge Kutta method.

TABLE 2

Parameters for the lumped parameter model of the venous and pulmonary circulations.

| Parameter | Symbol | Value |
|---|---|---|
| systemic venous compliance | $C_v$ | 0.075 cm$^5$/dyn |
| systemic venous resistance | $R_v$ | 13.3 dyn-sec/cm$^5$ |
| right heart outflow resistance | $R_{ro}$ | 4.0 dyn-sec/cm$^5$ |
| pulmonary artery compliance | $C_{pa}$ | 0.0032 cm$^5$/dyn |
| pulmonary artery resistance | $R_{pa}$ | 106.66 dyn-sec/cm$^5$ |
| pulmonary venous compliance | $C_{pv}$ | 0.0063 cm$^5$/dyn |
| pulmonary venous resistance | $R_{pv}$ | 13.33 dyn-sec/cm$^5$ |

2. Parameter estimation. Here, one embodiment of the method of parameter estimation, or the estimation of patient hemodynamic parameters from non-invasive measurements, is described.

Some previous work has been done on the use of parameter estimation techniques for analysis of the cardiovascular system. A recent publication applies system identification to a three element Windkessel model of the arterial system using pressure-dependent compliance (Capello et al., 1995). This is done by separating out mathematically the effects of the resistances from the compliance and then solving for each individually from measured canine arterial pulse data. Additional studies have been preformed to estimate arterial compliance, also based on a Windkessel approximation of the arterial tree (Laskey et al., 1990). Other prior art deals with linearized models, lumped-parameter models, or models of the arterial system or heart individually, but not in a Coupled manner.

In the presently proposed embodiment, the hemodynamic parameters are estimated using techniques similar to those of Yesilyurt and Patera (1995). If a parameter space can he defined for N influential model parameters which affect the behavior of the arterial system, then an objective function which gives an indication of the error between the output of the model for a given parameter set and the actual patient data can be defined. The terms "model output" and "patient data" refer to the pressure and velocity tracings versus time as measured at various anatomical locations throughout the body or the numerical model and the in-vivo case, respectively. If a random sampling of the N-parameter space is performed, surrogates which help to describe the "error" as a function of the parameters can he constructed using the N-dimensional interpolation scheme. From the polynomial fit, the "best fit" can be located and the corresponding parameters associated with the point of minimum "error" extracted. This procedure depends on the ability to generate enough points to obtain a representative samplings of the entire parameter space from which physiological behavior is expected to result. Additionally, it depends on the fact that a unique solution can be obtained, when several solutions may in fact exist. Another implication of sampling the parameter space is that as the number of parameters N increases, the number of required sample points increases exponentially (as does the time needed to accomplish all of the necessary computational runs).

3. Parameter Identification. It is technically possible to identify thousands of parameters associated with the numerical model. The prospect of attempting to determine exact behavior for a system with thousands of degrees of freedom, however, is an impossible task. Thus in order to accomplish the present objectives, certain simplifying assumptions are made, based on sell-similarity, parameter screening to identify the most critical parameters, dimensional analysis to express all the parameters in dimensionless form, a simplification of the model by elimination of all venous and pulmonary circulation elements, and other approximations, the number of critical parameters that exert the strongest influence on the solution is reduced to those in Table 3.

Using a grid discretized into four points along each axis, this results in a total of $4^6$ or 4096 runs. Among these cases, many combinations produce results that are unrealistic in that the predicted cardiac output or mean arterial pressure is too low. To identify and eliminate these cases, a simple lumped parameter model of the circulation is used to make a rough prediction of the solution, from which a determination is made as to whether or not to run the full, non-linear simulation for that particular set of parameter values. This procedure reduced the number of simulations to be run from 4096 to 337.

Thus, unique sets of the six parameters from Table 3 on a 4×4×4×4×4×4 grid were identified, where each axis was bounded by the maximum and minimum values selected for each individual parameter. Each axis was discretized into four nodes and each parameter assigned a dimensionless scale value of 0.0, 0.33, 0.66, and 1.0. The 337 grid points that fell within the physiological space were run and the data for the state variables as a function of time were stored for one steady-state cycle. The specified parameter set for each of the 337 runs was also stored for later processing The data from the 337 runs were used to construct the parameter space library from which surrogates were subsequently venerated. Thus, the model is no longer required following, construction of the surrogates, unless in the future additional modifications are required to increase the accuracy of the estimation method, which is in turn a function of the accuracy of the simulations.

As mentioned above, many possible methods exist to characterize the shape of the curve so as to allow comparison to other similar curves, and any of these procedures would be appropriate in the present case.

TABLE 3

The six parameters selected for parameter estimation.

| # | Dimensionless Form | Description |
|---|---|---|
| 1 | $\tilde{f} = \dfrac{fc_o}{L}$ | Heart rate |
| 2 | $\tilde{E}_{lv,max} = \dfrac{L^3 E_{lv,max}}{\rho c_o^2}$ | Peak left ventricle elastance |
| 3 | $E\hat{D}V = \dfrac{EDV}{L^3}$ | End diastolic volume |
| 4 | $\Omega = \tau_s \cdot f$ | Ejection period |
| 5 | $\tilde{P}_v = \dfrac{P_v}{\rho_o^2}$ | Central venous pressure |
| 6 | $\Phi$ and $R_s$ where $\dfrac{\Phi R_s}{L} = $ constan | Peripheral resistance |

Figure 4A:
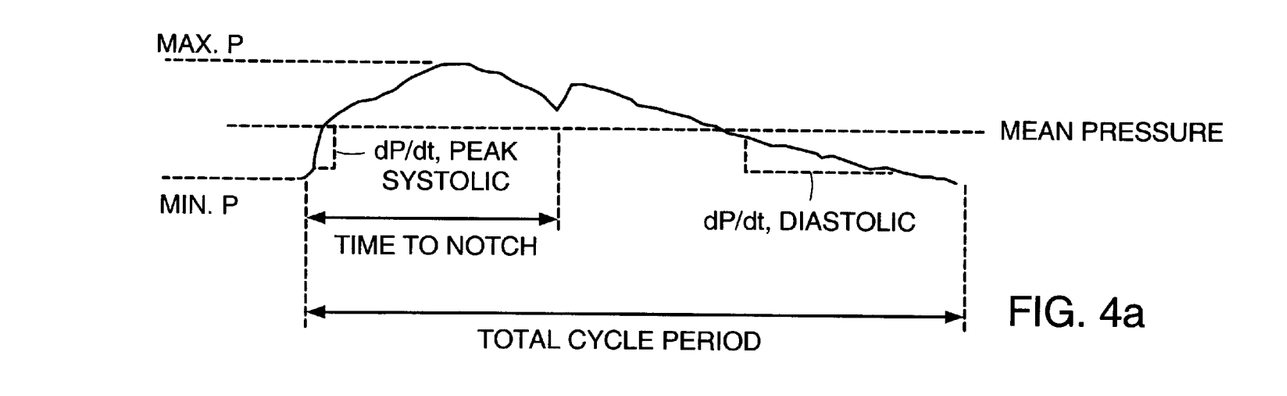
FIGS. 4a and 4b are graphical representations of feature extraction using data associated with a computed aortic pressure pulse (a) and a radial pressure pulse (b) as examples.
Figure 4B:
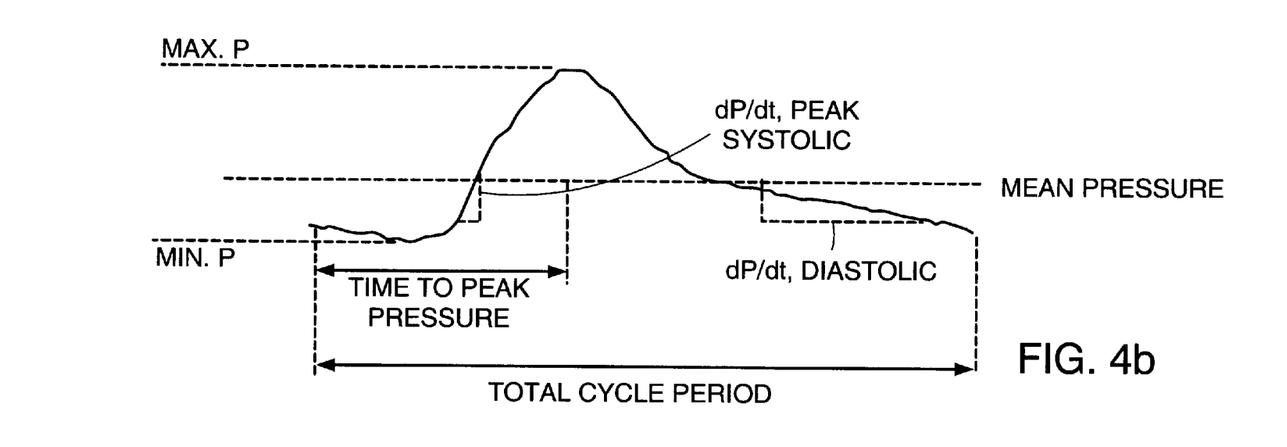

4. Feature Extraction. In the preferred embodiment, the solution for the unknown parameters is treated as a series of six equations with six unknowns (the six hemodynamic parameters in Table 3). It one considers the complexity of the pressure pulse, the six independent characteristics or features of the pulse can conceivably be extracted and quantified. Such a process is termed feature extraction to distinguish it from parameter estimation. A feature may take the form of any value that can be used to quantity the pulse. One must therefore make the assumption that each pulse is specific for each given set of parameter values, and therefore that six features are adequate to uniquely specify one pulse. Thus, the six equations developed using the Shepard routine (described below) become the dependance of each of the six features on the set of six parameters. The features employed in the present embodiment are those indices most often used by physicians. These include mean pressure, peak systolic dP/dt, the slope of the pressure upstroke during early systole, and the systolic ejection period, or the time during the cardiac cycle that the left ventricle is actively contracting. One can also envision several more features that would be expected to chancre as a function of the hemodynamic parameters: the peak pressure, the pressure at end diastole, dP/dt during diastole, the time to peak pressure, the time to the dicrotic notch, and so forth. Additional features such as the amplitude and timing of secondary and reflected peaks may also be included, although a systematic measurement these features is difficult and unreliable, as not all pressure pulses measured at different times or different locations may contain such information. The velocity waves at various locations may also be analyzed in similar manner, although it is less clear what features may follow the alterations in parameter values. These features and the concept of "feature extraction" are summarized graphically in FIGS. 4a and 4b.

The features selected should he functions of the six parameters, and should be as independent from each other as possible. They should also be representative of the system as a whole, rather than depend primarily upon local hemodynarnic conditions. One is not restricted. however, to using physical features that are visually obtained. Any six indices used to define a specific curve can be used. For instance, it may be possible to uniquely define a specific curve through the first several coefficients from the Fourier decomposition of a curve. Other mathematical decompositions may be applied to extract similar infromation. For present purposes, the set of Icatures used are those outlined in FIGS. 4a and 4b, applied to the radial artery and carotid artery pressures.

5. Surrogate generation. While it is clearly possible to calculate sample "points" throughout the parameter space values of the objective function, sparse points in space are inadequate for describing the complete behavior of the objective function. One can, however. make an estimation of a continuous function that describes the relationship between the objective function and the set of parameter values. This continuous function is called a "surrogate", and acts as a model for the functional relationship that we wish to estimate. The surrogate is a multidimensional interpolation of a field of sample points. An existing quadratic interpolation routine known as the Shepard quadratic interpolation can be implemented with little modification to the problem at hand. The original formulations were first described in detail by Franke and Nielson and Renka for the two and three dimensional cases (Franke and Nielson, 1990, Renka, 1988). Yesilyurt ( 1995) expanded the routine to arbitrary dimensions, following the formulation of Renka. Given that we have a data set D which contains N input-output pairs:

$$D = \{(P_1, f_1), \ldots, (P_1, f_n)\} \quad (28)$$

where $f_j$ is the feature value for a given set of parameter $p_j$, j=1. . . N:

$$f_j = F(p_j) j=1\ldots N \quad (29)$$

and where n is the total number of parameters in p. Thus, an interpolation function of the following from may be delined:

$$\tilde{F}(p) = \sum_{k=1}^{N} W_k(p) Q_k(p) \quad (31)$$

where $Q_k(p)$ are quadratic nodal functions acting as local approximations to F(p) of the form:

$$Q_k(p) = f_k + \left( \sum_{i=1}^{n} c_k^i (p^i - p_k^i) \right) + \sum_{j=1}^{n} \sum_{m=1}^{n} c_k^{\lambda(j,m;n)} (p^j - p_k^j)(p^m - p_k^m) \quad (32)$$

where:

$$\lambda(j, m; n) = m + \sum_{p=1}^{j} (n - j + p) \quad (33)$$

$$M \equiv \lambda(n, n; n) = n + \frac{(n)(n+1)}{2} \quad (34)$$

Equation (31) also contains the functions $W_k(p)$ which are normalized inverse-distance weights given by:

$$W_k(p) = \frac{W_k^*(p)}{\sum_{k=1}^{N} W_k^*(p)} \quad (35)$$

where $$W_k^*(p) = \left[ \frac{(R_w(p_k) - d_k(p))_+}{R_w(p_k) d_k(p)} \right]^2 \quad (36)$$

$$(R_w(p_k) - d_k(p))_+ = \begin{cases} R_w(p_k) - d_k(p) & \text{if } d_k(p) < R_w(p_k) \\ 0 & \text{otherwise} \end{cases} \quad (37)$$

In equation (36) $d_k(p)$ is the distance between point $p_k$ and p, and $R_w(p_k)$ is the radius influence about the node $p_k$.

The Shepard routine can be implemented to first determine the coefficients for the surrogate using the sample runs generated by the cardiovascular model. Thus, a set of parameters may be sent to the code, which then returns a single value based upon the interpolation between points, since any given set of parameters will lie in between grid points.

The routine flits well into the context of feature extraction, since we are interested in determining the behavior of each feature as a function of the unknown parameters. Thus, from expression (29), the variable $f_j$ corresponds to the jth feature, where j=1 . . . 6 tfor the case of the solution for 6 features with 6 unknown parameters. The feature $f$ is a function of the parameter set p, and thus an approximation to the relationship between feature and parameter set can be constructed. Thus, a value for the desired feature is extracted numerically from each individual library run, and stored with the set of parameters that were used as the input for that run. One therefore obtains 337 parameter sets and 337 values for one feature, which is then sent to the Shepard routine tfor the construction of the surrogate function. This process is repeated for each feature. From the set of all possible defined features, 6 are then selected as the functions from which a simultaneous solution can be obtained. However, since the series of equations are only interpolations and cannot be solved explicitly, an iterative scheme must be implemented to determine the solution.

6. Solving for Parameters. The commercial software package MATLAB contains a toolbox for optimization. Since MATLAB is capable of executing UNIX commands interactively, one may use six surrogates defined by the Shepard routine to act as a function for the minimizer tool. The tool passes a set of parameters to the user defined function containing the surrogate information, and is returned a value corresponding to the "closeness of fit." Since the assumption has been made that a set of features corresponds to one unique set of parameters only, then the best fit will be achieved when a set of parameters yields a set of feature values that is identical to the feature set of the test case (i.e. the patient data). That is, if the feature set from the patient is a vector $F_p$, and the set from the surrogates is also a vector $F_s$, where $F_s=F_s(P)$, then the distance $|F_p-F_s|$ becomes smaller than some predelined error, corresponding to the solution parameter set p. This provides a systematic framework for the parameter estimation scheme.

Figure 5:
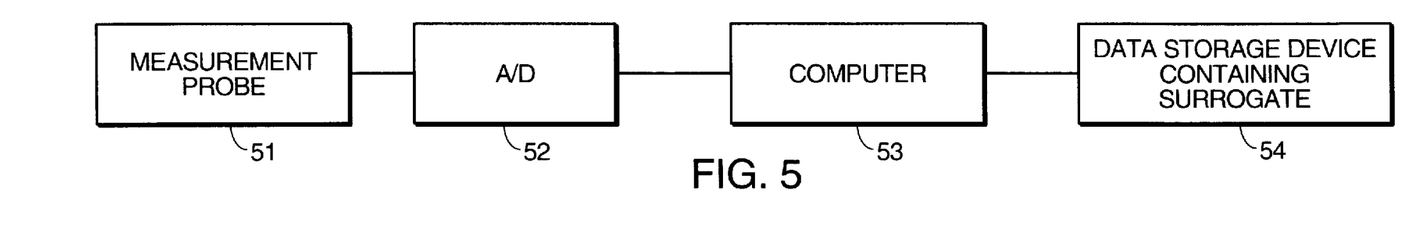
FIG. 5 is a block diagram of the device elements in accordance with a specific embodiment of the invention.

7. Implementation. FIG. 5 shows that, in one embodiment, the device includes a measurement probe 51, which may be implemented, for example, by either a pressure monitor for measuring the arterial pressure trace or a Doppler flow probe for measuring time-varying flow velocity, and an analog-to-digital converter 52 connected to a computer 53. The computer 53 has a data storage device 54 containing the surrogate representation of the functional relationships between the features of the simulated pressure or flow trace and the model parameters.

Figure 6:
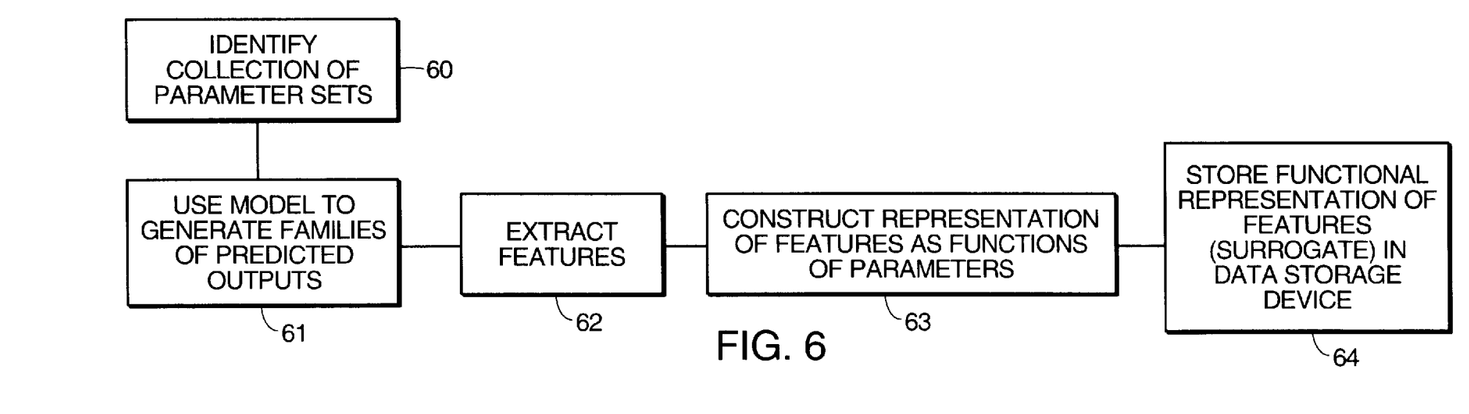
FIG. 6 is a block diagram of surrogate creation in accordance with an embodiment of the invention.

The surrogate may be created by the steps shown in FIG. 6. The first stop 60 involves identifying a collection of parameter sets that span the pertinent physiologic range (see Section 3. Parameter Identification). The next step 61 involves using these parameter set as input to the computational model to generate simulated pressure or flow traces, referred to here as predicted outputs, that are analyzed in step 62 to extract values for the features of each trace (see Section 4, Feature Extraction). Each feature is a function of the model parameters. In step 63, the computed features at discrete values of the parameters are represented by continuous functions, termed the surrogate using various curve-fitting methods such as the Shepard routine (Franke and Nielson, 1990, Renka, 1988), represented by equations (31)–(37) (see Section 5, Surroate Extraction). In step 64, the numerical coefficients that describe the functional dependence of the features on the parameters are then saved in the storage medium 54.

Figure 7:
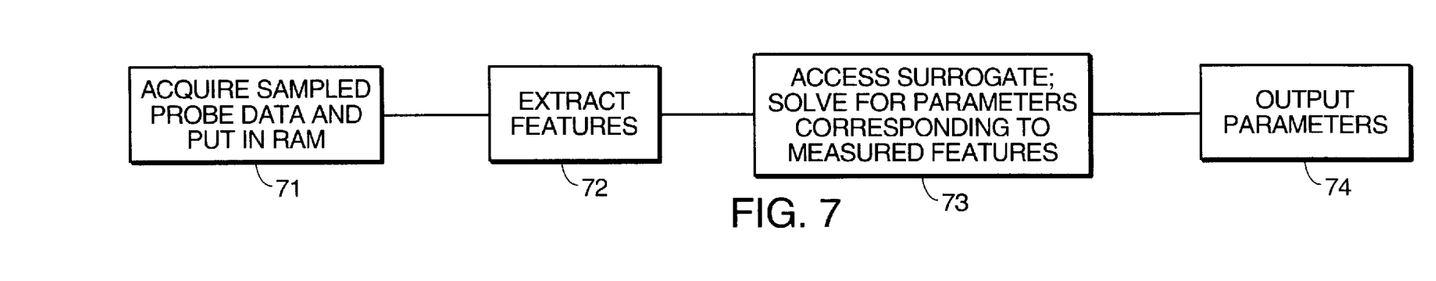
FIG. 7 is a block diagram of device operation in accordance with an embodiment of the invention.
Figure 8:
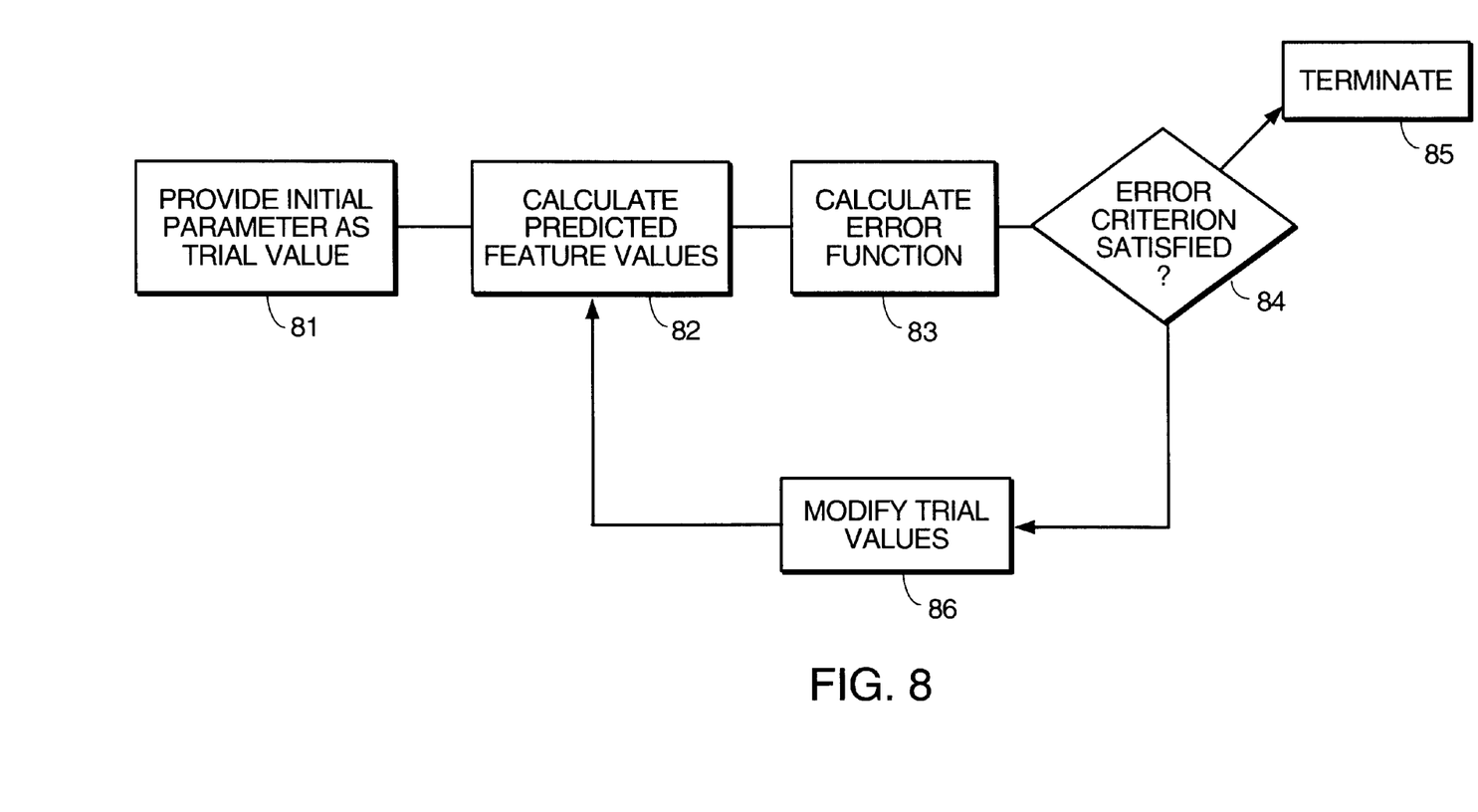
FIG. 8 is an illustration of how parameters are computed according to an embodiment of the invention.

The operation of a device in accordance with a preferred embodiment of the invention is illustrated in FIG. 7. The measurement sample acquired with the probe 51 is first stored (in step 71) in RAM. In step 72, the stored measurement sample is accessed by the computer 53 to perform feature extraction, that is, the calculation of feature values. In step 73, the computer then accesses the coefficient matrices ($C_k^i$ and $C_k^{l(j,m;n)}$ in equation (32)), constituting the surrogate, to solve for the parameter values that correspond to the measured features. In step 74. the parameter values are provided as an output; the output parameters describe the physiological state of the subject FIG. 8 illustrates one method by which the computer 53 may solve for the parameters 73. (See also Section 6, Solving for Parameters.) In step 81, a set of parameter values is first chosen at random, and in step 82 the surrogate is used to calculate the predicted feature values. In step 83, these computed features are compared to the values extracted from the experimental measurement 72 and a measure of the error or difference between the two sets is obtained. In step 84. a test is performed, and if this error is small enough to meet some predetermined criterion. the procedure deems the fit to be good and in step 85 provides as output the corresponding set of parameter values. It in step 84 the error criterion is not met, the trial values are modified in stop 86 and now feature values are computed again in stop 82. This process continues until such time as the error criterion is satisfied and the cycle terminates with a solution in stop 85.

Bibliography

Berger. D. S., Li, J. K-J. Noordergral, A. Differential effects of wave reflections and peripheral resistance on aortic blood pressure: a model-based study. *Am. J. Phyviol.* 266 (*Heart Circ. Physisol.* 35): H1626–H1642, 1994.

Berger, D. S., Li, J. K-J, Noordergraf, A. Arterial Wave Propagation Phenomena, Ventricular Work, and Power Dissipation. *Annals of Bioinedicol Engieering*, Vol. 23, 164–177, 1995.

Cappello, A., Gnudi, G., Lamberti, C. Identification of the Three-Element Windkessel Model Incorporating a Pressure-Dependant Compliance. *Annals of Biomedical Engineering*. Vol. 23, 164–177, 1995.

Collins, J. M., Shapiro, A. H., Kimmel, E., and Kammn, R. D. The Steady Expiratory Pressure-Flow Relation in a Model Pulmonary Bifurcation. *Journal of Biomedical Engineering*. 115:299–305, 1993.

Franke, R., Nielson, G. M. Scattered data interpolation and applications: A tutorial and study, in: H. Hagen and D. Roller, eds., *Geometric Modeling: Methods and Applications*. (131–16). Springer-Verlag, Berlin, 1990.

Fung, Y. C. Stress-strain-history relations of soft tissues in simple elongation. In: Biomechanics, its foundations and objectives. Y. C. Fung, N. Perrone, M. Anliker (eds.), Prentice-Hall, Englewood Cliff's, 1972.

Holenstein, R., Niederer, P., and Anliker, M. A Viscoelastic Model for Use in Predicting Arterial Pulse Waves, *Journal of Biomechanical Engineering*. 102, 318–325, 1980.

Kimmel, E., Kamm, R. D., and Shapiro, A. H. Numerical Solutions for Steady and Unsteady Flow in a Model of the Pulmonary Airways. *Journal of Biomechanical.* 110 (292–299), 1988.

Laskey, W. K., et al, Estimation of total systemic arterial compliance in humans. *J. Appl. Physisol,* 69(1):112–119, 1990.

Mills, C. J., et al. Pressure-flow relationships and vascular impedance in man, Cardiovascular Research, 4, 405–417, 1970.

Niederer, P. Damping mechanisms and shock transitions in the human arterial tree. *Journal of Applied Mathematics and Physics.* 36. 204–220, 1985.

Ozlawa, E., Ph.D. "A model-based method from estimating hemodynamic parameters", Dissertation, MIT, 1996.

Pedley, T. J. *The Fluid Mechanics of Large Blood Vessels.* Cambridge University Press, 1980.

Pedley, T. J., Schroter, R. C. and Sudlow, M. F. Energy losses and pressure drop in models of human airways. Resp. Physiol., 9:371–386, 1970.

Renka, R. L. Algorithm 660: QSHEP2D: Quadratic Shepard method for bivariate interpolation of scattered data. ACM TOMS, 14, (149–15), 1988.

Stettler, J. C., Niederer, P. and Anliker, M. Theoretical analysis of arterial hemodynamics including the influence of bifurcations. Part I: Mathematical Model and Prediction of Normal Pulse Patterns. *Annals of Biomecical Engineering.* 9(145–164), 1981.

Suga, H. and Sagawa, K. Instantaneous Pressure-Volume Relationships and Their Ratio in the Excised, Supported Canine Left Ventricle. *Circulation Research,* Vol 35, July 1974.

Wolf, T. *An Experimental/Theoretical Investigation of Parallel Inhomogeneities in Respiratory Flows.* Ph.D. thesis, Dept. of Mechanical Engineering, Massachusetts Institute of Technology: June, 1990.

Yesilyuirt, S. *Construction and validation of computer-simulation surrogates for engineering design and optimization.* Ph.D. thesis, Dept. of Mechanical Engineering. Massachusetts Institute of Technology: April, 1995.

Yesilyurt, S., Patera, A. T. Surrogates for numerical simulations: optimization of eddy-promoter heat exchangers.

*Computer Methods in Applied Mechanics and Engineering* 121. 231–257, 1995.

Zeilke, W. Frequency-Dependent Friction in Transient Pipe Flow. *Journal of Basic Engineering.* 90, series D, No. 1, 109 (1968).

We claim:

1. A method of deriving a physiological description of a cardiovascular system, the method comprising:
   a. obtaining a measurement sample associated with flow of the cardiovascular system, and
   b. utilizing a model that predicts, from first principles, measurement values associated with cardiovascular blood flow as a function of a plurality of source parameters, the model not being, an empirically-based construct, to derive a physiological description of the cardiovascular system in terms of at least one of the source parameters, wherein the model is at least one of (i) distributed and (ii) non-linear.

2. A method of deriving a physiological description of a cardiovascular system, the method comprising:
   a. obtaining a measurement sample associated with flow of the cardiovascular system,
   b. matching the measurement sample against a library of stored predicted samples, each predicted sample derived from first principles from a model of the cardiovascular system and associated with a set of source parameter values, the model not being an empirically-based construct, the set having at least one source parameter value, to identify a best-matching predicted sample, and
   c. associating the measurement sample with the set that is associated with the best-matching, predicted sample.

3. A method according to claim 2, wherein the model is at least one of non-linear and distributed.

4. A method according to claim 2, wherein the set is selected to provide a physiologically useful description of the cardiovascular system.

5. A method according, to claim 2, wherein the set includes a source parameter that provides a measure of compliance of the heart during contraction.

6. A method according to claim 2 wherein the set includes a source parameter that provides a measure of systemic vascular resistance.

7. A method according to claim 2, wherein the set includes a source parameter that provides a measure of cardiac output.

8. A method according to claim 2, wherein b. further includes:
   (1) determining a score for the closeness of the match between the measurement sample and each of a plurality of stored samples, and
   (2) selecting the best-matching sample based on the score.

9. An apparatus for deriving a physiological description of a cardiovascular system, the apparatus comprising:
   a. input means for receiving a measurement sample associated with flow of the cardiovascular system;
   b. processor means coupled to the input means and utilizing a model that predicts, from first principles, measurement values associated with cardiovascular blood flow as a function of a plurality of source parameters, the processor means for deriving the value of at least one source parameter pertinent to a physiological description of the cardiovascular system, wherein the model is at least one of (i) distributed and (ii) non-linear and is not an empirically-based construct; and
   c. output means for specifying the value of the at least one source parameter.

10. An apparatus for deriving a physiological description of a cardiovascular system, the apparatus comprising:
    a. input means for receiving a measurement sample associated with flow of the cardiovascular system;
    b. digital storage means for storing a library of predicted samples, each predicted sample derived from first principles from a model of the cardiovascular system and associated with a set of source parameter values, the model not an empirically-based construct, the set having at least one source parameter value;
    c. processor means coupled to the input means and having access to the digital storage means for matching the measurement sample against the library of predicted samples to identify a best-matching predicted sample; and
    d. output means for identifying at least one member of the set of source parameter values associated with the best-matching predicted sample.

11. An apparatus according to claim 10, wherein the model is at least one of non-linear and distributed.

12. An apparatus according to claim 10, wherein the set is selected to provide a physiologically useful description of the cardiovascular system.

13. An apparatus according to claim 10, wherein the set includes a source parameter that provides a measure of compliance of the heart during contraction.

14. An apparatus according to claim 10, wherein the set includes a source parameter that provides a measure of systemic vascular resistance.

15. An apparatus according to claim 10, wherein the set includes a source parameter that provides a measure of cardiac output.

16. An apparatus according to claim 10, wherein the processor means includes an arrangement for determining a score for the closeness of the match between the measurement sample and each of a plurality of stored predicted samples and for selecting the best-matching sample based on the score.

* * * * *